United States Patent [19]

Yamanishi et al.

[11] Patent Number: 4,695,540
[45] Date of Patent: * Sep. 22, 1987

[54] QUANTITATIVE DETERMINATION OF SUBSTRATE TREATED WITH OXIDASE

[75] Inventors: Kazuhiko Yamanishi, Tokyo; Toshiro Hanada, Kawagoe, both of Japan

[73] Assignee: Wako Pure Chemical Industries, Ltd., Osaka, Japan

[ * ] Notice: The portion of the term of this patent subsequent to Sep. 22, 2004 has been disclaimed.

[21] Appl. No.: 516,271

[22] Filed: Jul. 22, 1983

[30] Foreign Application Priority Data

Jul. 23, 1982 [JP] Japan .................................. 57-128700
Jun. 20, 1983 [JP] Japan .................................. 58-110423

[51] Int. Cl.$^4$ ..................... C12Q 1/62; C12Q 1/60; C12Q 1/54; C12Q 1/26; C12Q 1/28
[52] U.S. Cl. ........................................ 435/10; 435/11; 435/14; 435/25; 435/28; 435/810
[58] Field of Search ................. 435/10, 11, 14, 25, 435/28, 817, 810

[56] References Cited

U.S. PATENT DOCUMENTS 4,353,983  10/1982  Siddiqi .................................. 435/13

FOREIGN PATENT DOCUMENTS 0054358  6/1982  European Pat. Off. .............. 435/28
0100217  2/1984  European Pat. Off. .............. 435/25
4058490  5/1979  Japan .................................... 435/25

OTHER PUBLICATIONS

Halliwell et al., (1982), Interaction of the Superoxide Radical with Peroxidase and with Other Non Complexes, Oxidase Relat Redox Syst Proc Int Symp, 3rd, 1979.

Stryer, L., (1975), Biochemistry, 2nd Ed., p. 344.

Porras et al., (1981), The Reaction of Reduced Xanthine Oxidase with Oxygen, J.Biol. Chem. 256(17): 9096–9103.

Matkovics et al., (1975), Utilization of Catalase and Superoxide Dismutase to Clarify the Mechanism of Action of Oxidases, Proc. Hung. Annu. Meet. Biochem. 15:95, Chem. Abstr. 88:46907w.

Galliani et al., (1980), Formation of Superoxide Radical Anion in the Horseradish Peroxides-Catalyzed Oxidation of three Aromatic Tertiary Amines with Hydrogen Peroxide, J. Chem. Soc. (1) 1–3, Chem. Abstr. 92:18038f.

*Primary Examiner*—Esther M. Kepplinger
*Attorney, Agent, or Firm*—Armstrong, Nikaido, Marmelstein & Kubovcik

[57] ABSTRACT

Cholesterol in a sample can be determined quantitatively by measuring colorimetrically superoxide ion generated by treating the sample with cholesterol oxidase. Similarly, a substrate such as glucose, etc., can be determined quantitatively by measuring the generated superoxide ion colorimetrically, said oxidase treatment and measuring of the generated superoxide ion being conducted by using a reagent composition comprising (a) an oxidase, (b') iron complex of porphyrin or ion chelate of complexane, (c) an amine and/or a phenol, (d) a thiol compound, (e) a color producing reagent to be reduced, and if necessary (f) a chelating agent.

6 Claims, 5 Drawing Figures

QUANTITATIVE DETERMINATION OF SUBSTRATE TREATED WITH OXIDASE

This invention relates to a process for quantitatively determining a substrate. More particularly, this invention relates to a process for quantitatively determining a substrate such as blood components applying an enzymic reaction in clinical chemical examinations and the like.

In quantitative determination of substrates by means of enzymes, particularly oxidases, the products by the enzymic reactions are water, carbon dioxide gas and hydrogen peroxide. Recently, the measurement of the produced hydrogen peroxide for quantitative determination of substrates has gained wide applications due to biochemical knowledge that enzymes have inherent specificity, that is, quantitativeness. As a result, chemical quantitative determinations previously used are hardly employed, since various devices are necessary for maintaining quantitativeness, corrosion of chemicals causes fatal problems, there are some problems in specificity, and the like. But recent enzymic processes are not always sufficiently satisfactory. This can be explained referring to quantitative determination of cholesterol as follows.

An increase of cholesterol causes hypercholesterolemia which is found in nephrosis syndrome, serious diabetes mellitus, dysthyroidism, glycogen accumulation disease, familial hyperlipemia, and the like. On the other hand, a decrease of cholesterol causes hypocholesterinemia which is found in serious liver disease, insufficient nutrition, hyperthyroidism, and the like. The quantitative determination of cholesterol is an essential test item in the field of clinical chemical examinations. As processes for quantitatively determining cholesterol, there were employed Zak-Henry's method and Zurkowsky method wherein the Liebermann-Burchard reaction and the Kiliani reaction were applied to a colorimetric reaction. But, after the proposal of a combination of an enzyme which oxidizes cholesterol to $\Delta^4$-cholestenon and hydrogen peroxide with a reagent for measuring the produced hydrogen peroxide, this enzymic process becomes a major process for quantitative determination of cholesterol. But this enzymic process still requires further improvements, since influences of reducing substances in body fluid cannot be prevented. Further, the sensitivity is insufficient and the use of oxidizable color producing reagents which can produce color at higher wavelength sides is required for improvement.

The present inventors had questions on previous knowledge that enzymic reactions caused by individual specific oxidases for various substrates simply produce final products such as water and hydrogen peroxide and studied enzymic reactions extensively with a hope that new applications can be obtained by studying enzymic reactions. After studies of various combinations of substrates in body fluid and oxidases showing specificity, it was found that superoxide ions were produced quantitatively by enzymic reactions of individual specific oxidases with substrates and said superoxide ions were changed to certain substances such as hydrogen peroxide and that the measurement of superoxide ions made it possible to determine quantitatively the substrates, and accomplished this invention.

This invention provides a process for quantitatively determining a substrate particularly cholesterol, which comprises treating a substrate with an oxidase and measuring the generated superoxide ion.

In the attached drawing.

Figure 1:
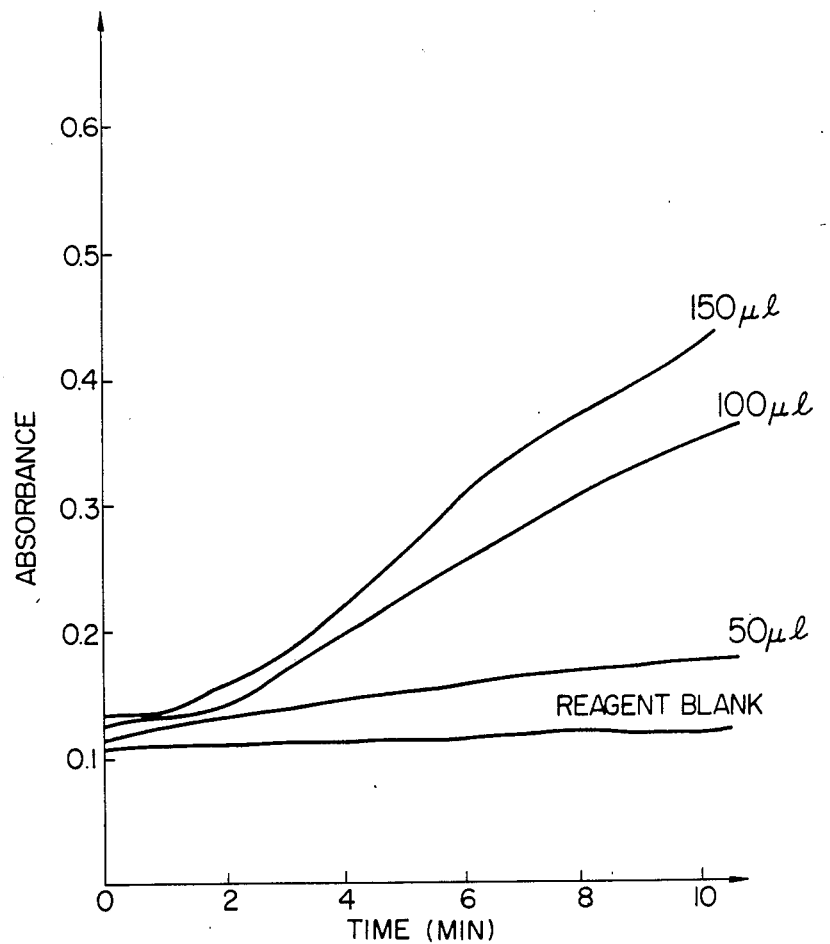
FIGS. 1 to 3 are graphs showing change of absorbance with the lapse of time.

According to this invention, there are many advantages in that a color producing reagent to be reduced can be used, there is no influence of reducing substances usually present in body fluid such as bilirubin and ascorbic acid, it is possible to use a color producing reagent to be reduced which has high sensitivity and can produce color at longer wavelength side, and the like. Thus, the process of this invention is very advantageous in clinical examinations.

The reaction according to this invention proceeds as follows:

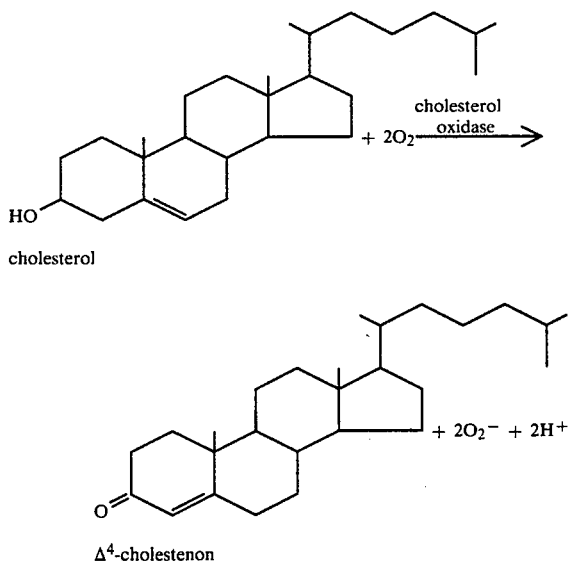

As shown above, superoxide ion ($O_2^-$) is produced by the enzymic action of cholesterol oxidase.

The produced superoxide ion is in usual easily converted into hydrogen peroxide and this reaction is accelerated by superoxide dismutase usually present in blood serum (T. Matsuura: Synthetic Chemical Series, Enzymic Oxidation Reaction, page 69, Maruzen Co., Ltd., 1977). In general, superoxide ion reacts with a color producing reagent to be reduced to form a color (Y. Oyanagi: Superoxides and Medical Science, pages 7-8, Kyoritsu Publishing Co. 1981), but the reaction is too slow to apply to quantitative determination of cholesterol in practical applications.

In order to block the change of superoxide ion to hydrogen peroxide and to accelerate the reaction with a color producing reagent to be reduced to form a color, a thiol compound such as reduced glutathione, mercaptoethanol, cysteine, or the like, peroxidase, and a phenol are used according to this invention. Thus, applying reducing properties of superoxide ion, cholesterol in body fluid can be determined quantitatively. That is, by measuring color formation or color change produced by reduction of a color producing reagent to be reduced by the superoxide ion, cholesterol in body fluid or in a sample can be determined quantitatively.

In the case of quantitative determination of cholesterol in body fluid sample, to a suitable medium containing body fluid to be tested, (a) cholesterol oxidase, (b) peroxidase, (c) a phenol, (d) a thiol compound, and (e) a color producing reagent to be reduced such as Nitrotetrazolium Blue (hereinafter referred to as "NO₂-TB") are added and incubated, and a color produced is determined colorimetrically. That is, the cholesterol in the body fluid sample is treated with cholesterol oxidase and the generated superoxide ion causes color to be formed by the color producing reagent to be reduced, and thus the cholesterol in the sample can be determined quantitatively.

During the above-mentioned examination, pH is maintained at 7.0 or higher, preferably 7.5 or higher.

As the color producing reagent to be reduced, tetrazolium compounds had various problems in that formazans produced by reduction of tetrazolium compounds are difficultly soluble in water, quantitativeness of color formation is not good, and devices are contaminated, and the like. But recent development obtained by introducing a group which improves the solubility into tetrazolium compounds solved such problems and makes it possible to employ these compounds in this invention.

Embodiments of this invention are explained in detail referring to the following experiments.

In order to confirm the production of superoxide ion by the enzymic action of cholesterol oxidase, the following experiments are conducted using cholesterol oxidase and NO₂-TB.

The reaction for producing superoxide ion by cholesterol oxidase and the confirmation reaction thereof are as follows:

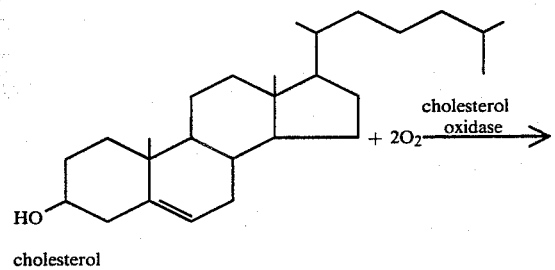

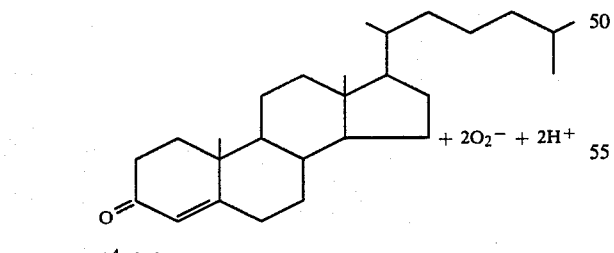

$$\text{NO}_2\text{—TB} + \text{Cl}^- + 2\text{O}_2^- + 2\text{H}^+ \longrightarrow$$
$$\frac{1}{2}\text{ diformazan} + 2\text{O}_2 + \text{HCl}$$

$$\left(\begin{array}{c}\text{Reduction of NO}_2\text{—TB by} \\ \text{superoxide ion}\end{array} \longrightarrow \begin{array}{c}\text{Formation of} \\ \text{diformazan}\end{array}\right)$$

EXPERIMENT 1

(Qualitative test)

Using cholesterol oxidase and NO₂-TB, coloring by superoxide ion are tested qualitatively.

Further, influences of change of pH and of addition of 1-methoxy-phenazine metosulfate (1-methoxy PMS), diaphorase, or reduced glutathione (hereinafter referred to as "GSH") are tested.

Reagents (1) Cholesterol solution

200 Mg of cholesterol is dissolved in isopropanol to make the volume 100 ml.

(2) Color producing reagent solution A

In 0.1M tris (precisely tris-HCl) buffer solution (pH 8.0), 150 units of cholesterol oxidase and 50 mg of NO₂-TB are dissolved and the whole volume is made 1000 ml.

(3) Color producing reagent solution B

To the color producing reagent solution A, 100 mg of reduced glutathione is added and the whole volume is made 1000 ml.

(4) Color producing reagent solution C

To the color producing reagent solution A, 30 mg of 1-methoxy PMS is added and the whole volume is made 1000 ml.

(5) Color producing reagent solution D

To the color producing reagent solution A, 2000 units of diaphorase is added and the whole volume is made 1000 ml.

(6) Color producing reagent solution E 0.1M tris buffer solution (pH 7.0) is used in the color producing reagent solution B in place of 0.1M tris buffer solution (pH 8.0).

(7) Hydrogen peroxide solution

There is prepared a 0.1% hydrogen peroxide solution.

(8) Isopropanol (IPA)

Experimental Method

Each 50 μl of the cholesterol solution is placed in 5 test tubes and each 3 ml of the color producing reagent solutions A, B, C, D, and E is added to each test tube and incubated in a constant temperature chamber at 37° C. for 10 minutes. Then, color formation is observed in comparison with the reagent blank. The results are as shown in Table 1.

TABLE 1

| Additive in color producing reagent solution | pH | Degree of coloring |
|---|---|---|
| None | 8 | x |
| GSH | 8 | o |
| 1-Methoxy PMS | 8 | x |
| Diaphorase | 8 | x |
| GSH | 7 | Δ |

Note
o: Color was produced.
x: Color was not produced.
Δ: Color was produced but weak.

As is clear from Table 1, the color is formed clearly only when GSH (reduced glutathione) is added and the reaction is conducted at pH 8.0.

FIG. 1 is a graph showing changes of absorbances with the lapse of time using the color producing reagent solution B and changing the amount of the cholesterol solution from 50 μl to 100 μl and 150 μl, subjected to the same reaction as mentioned above, and obtained by measuring the absorbances at wavelength of 560 nm.

Figure 2:
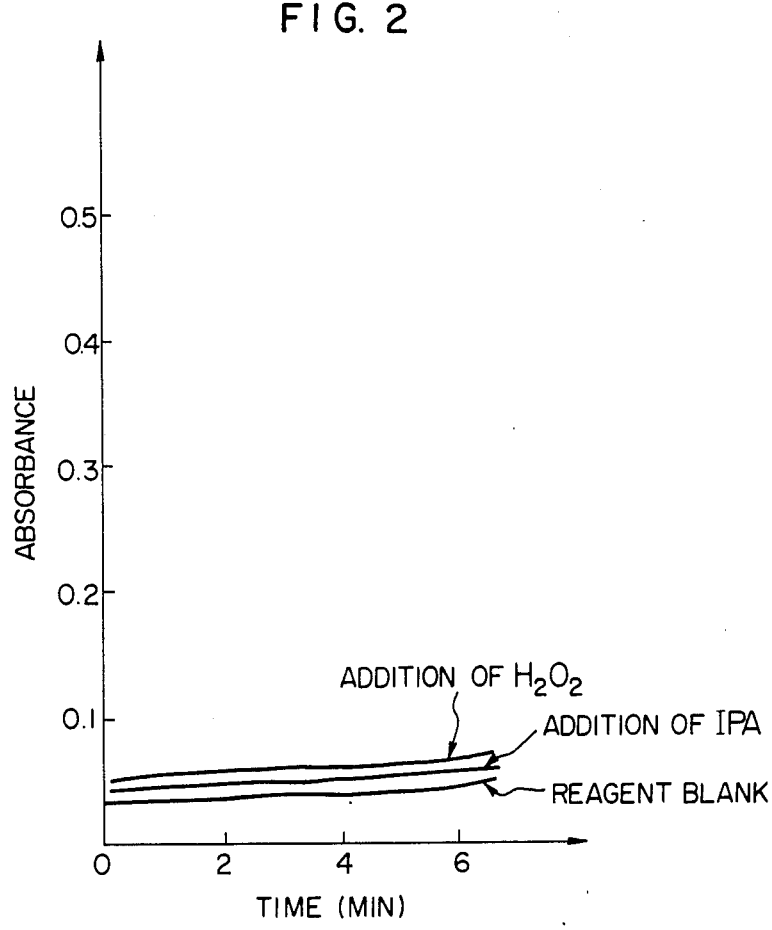

FIG. 2 is a graph showing changes of absorbances with the lapse of time using the color producing reagent solution B and the hydrogen peroxide solution or IPA in place of the cholesterol solution, obtained in the same manner as in FIG. 1.

As is clear from FIGS. 1 and 2, it is confirmed that the coloring is caused by the superoxide ion.

EXPERIMENT 2

Effects of Addition of Peroxidase, Phenol

Reagents (1) Cholesterol solution
The same as in Experiment 1.

(2) Color producing reagent solution F
In 0.1M tris buffer solution (pH 8.0), 150 units of cholesterol oxidase, 100 mg of $NO_2$-TB and 100 mg of GSH are dissolved and the whole volume is made 1000 ml.

(3) Color producing reagent solution G
To the color producing reagent solution F, 6000 units of peroxidase is added and the whole volume is made 1000 ml.

(4) Color producing reagent solution H
To the color producing reagent solution G, 1 g of phenol is added and the whole volume is made 1000 ml.

Experimental Method

To 50 μl of the cholesterol solution, each 4 ml of the color producing reagent solutions F, G, and H is added and mixed, followed by incubation in a constant temperature chamber at 37° C. for a predetermined time (10 minutes). Then, absorbances at wavelength of 560 nm are measured using the reagent blank as control. The results are shown in FIG. 3, wherein changes of absorbances with the lapse of time are plotted.

Figure 3:
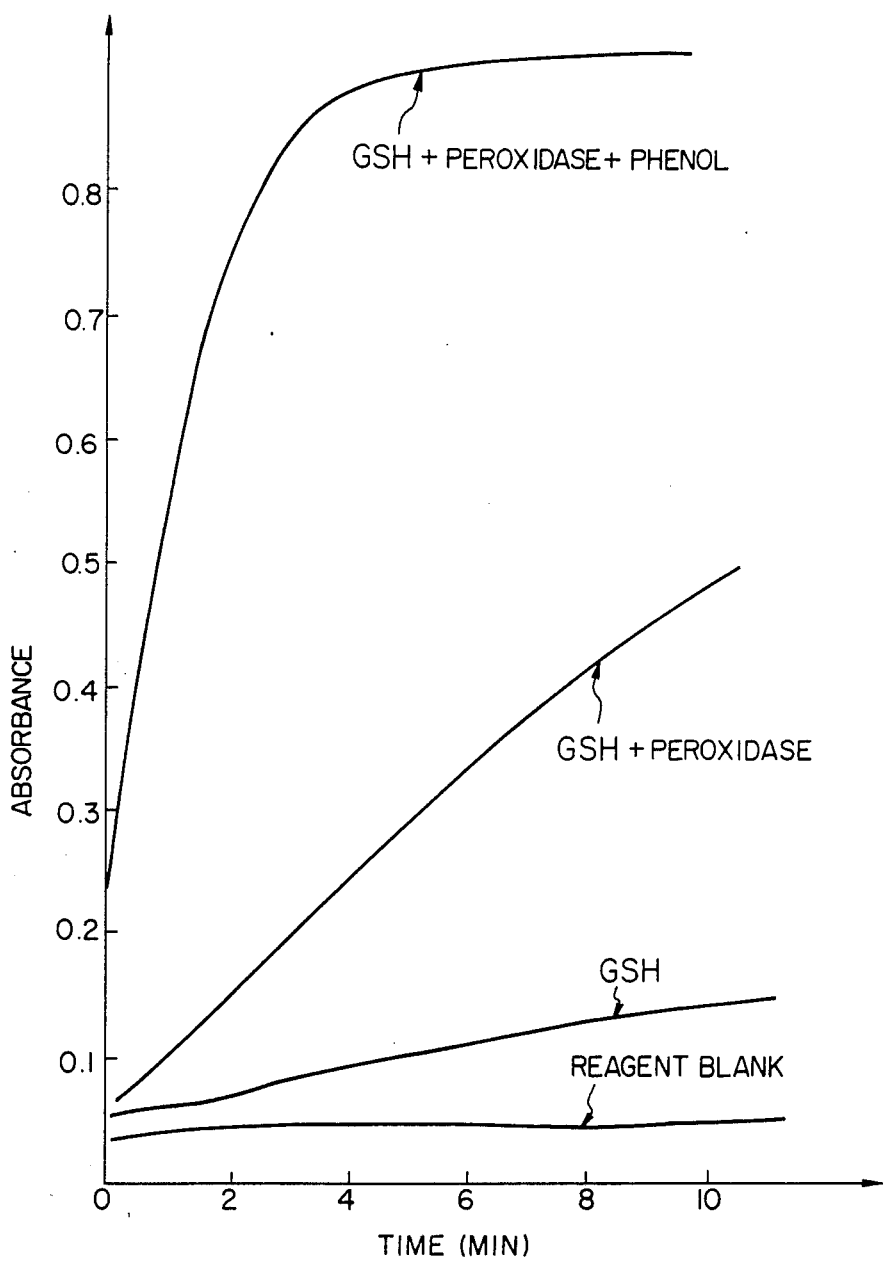

As is clear from FIG. 3, the addition of both peroxidase and phenol makes the reaction faster and the maximum coloring can be obtained after 4 to 6 minutes. Such an effect can be admitted when only peroxidase is added.

EXPERIMENT 3

Since the reaction is accelerated by the addition of peroxidase and phenol and the coloring is stable, calibration curves are obtained by changing the cholesterol concentration. Further, the amount of $NO_2$-TB in reagents solutions is changed and compared.

Reagents (1) Standard solutions
Standard solutions are prepared by dissolving 40 mg, 80 mg, 120 mg, 160 mg and 200 mg of cholesterol in isopropanol and making the volume 100 ml, respectively.

(2) Color producing reagent solution I
In 0.1M tris buffer solution (pH 8.0), 150 units of cholesterol oxidase, 100 mg of GSH, 6000 units of peroxidase, 1 g of phenol, and 100 mg of $NO_2$-TB are dissolved and the whole volume is made 1000 ml.

(3) Color producing reagent solution J
The amount of $NO_2$-TB in the color producing reagent solution I is changed to 200 mg from 100 mg.

Experimental Method

To each 50 μl of the standard solutions, each 4 ml of the color producing reagent solutions I and J is added, followed by incubation in a constant temperature chamber at 37° C. for 10 minutes. Then, absorbances at wavelength of 560 nm are measured using reagent blank as control.

Figure 4:
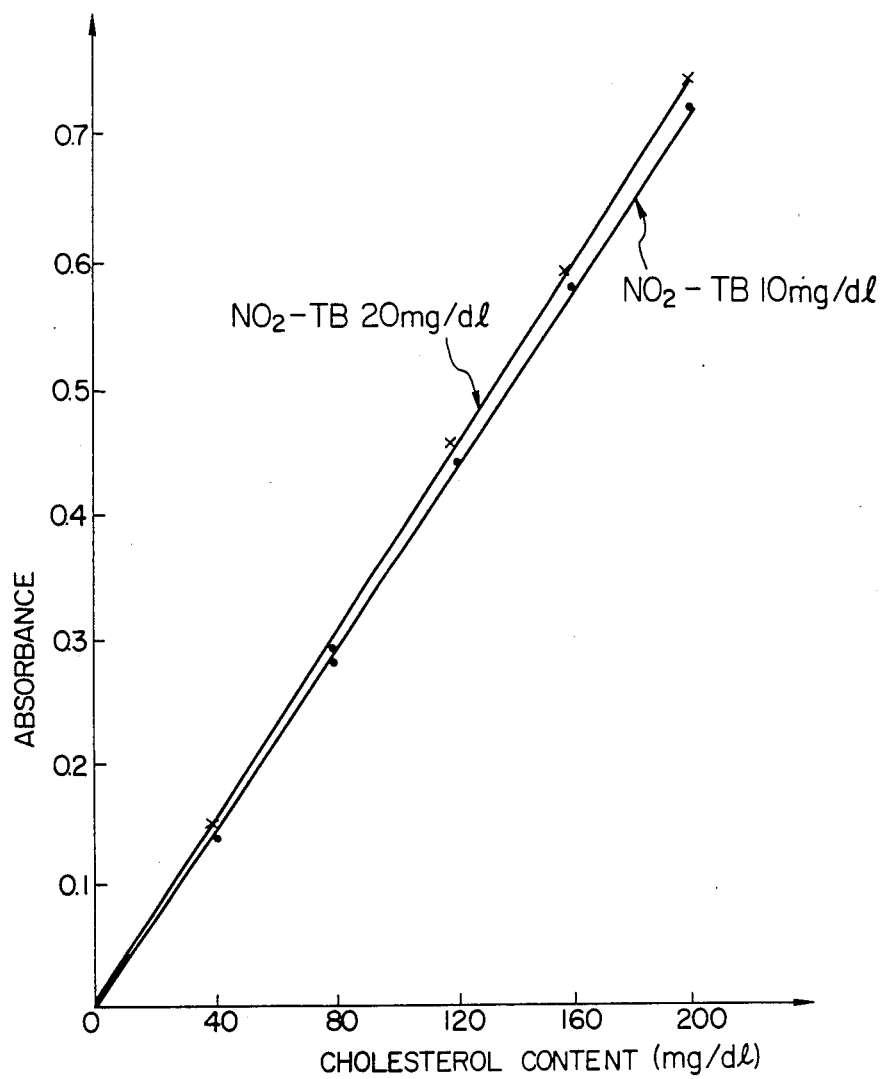
FIG. 4 shows calibration curves.

The results are shown in Table 2. FIG. 4 shows calibration curves.

As is clear from FIG. 4, linearity is shown at the $NO_2$-TB concentrations of 10 mg/dl and 20 mg/dl.

TABLE 2

| Cholesterol concentration | $NO_2$ - TB concentration | |
|---|---|---|
| | 10 mg/dl | 20 mg/dl |
| 40 mg/dl | 0.143 | 0.147 |
| 80 | 0.280 | 0.298 |
| 120 | 0.446 | 0.459 |
| 160 | 0.582 | 0.596 |
| 200 | 0.721 | 0.741 |
| Reagent blank | 0.013 | 0.021 |

EXPERIMENT 4

Absorption Curve and Sensitivity

Reagents (1) Cholesterol solution
The same as in Experiment 1.

(2) Color producing reagent solution K
In 0.1M tris buffer solution (pH 8.0), 150 units of cholesterol oxidase, 100 mg of GSH, 6000 units of peroxidase, 1 g of phenol and 200 mg of $NO_2$-TB are dissolved and the whole volume is made 1000 ml.

Experimental Method

To 50 μl of the cholesterol solution, 4 ml of the color producing reagent solution is added and mixed, followed by incubation in a constant temperature chamber at 37° C. for 10 minutes. Then, absorbance at wavelength of 400 to 700 nm is measured.

Figure 5:
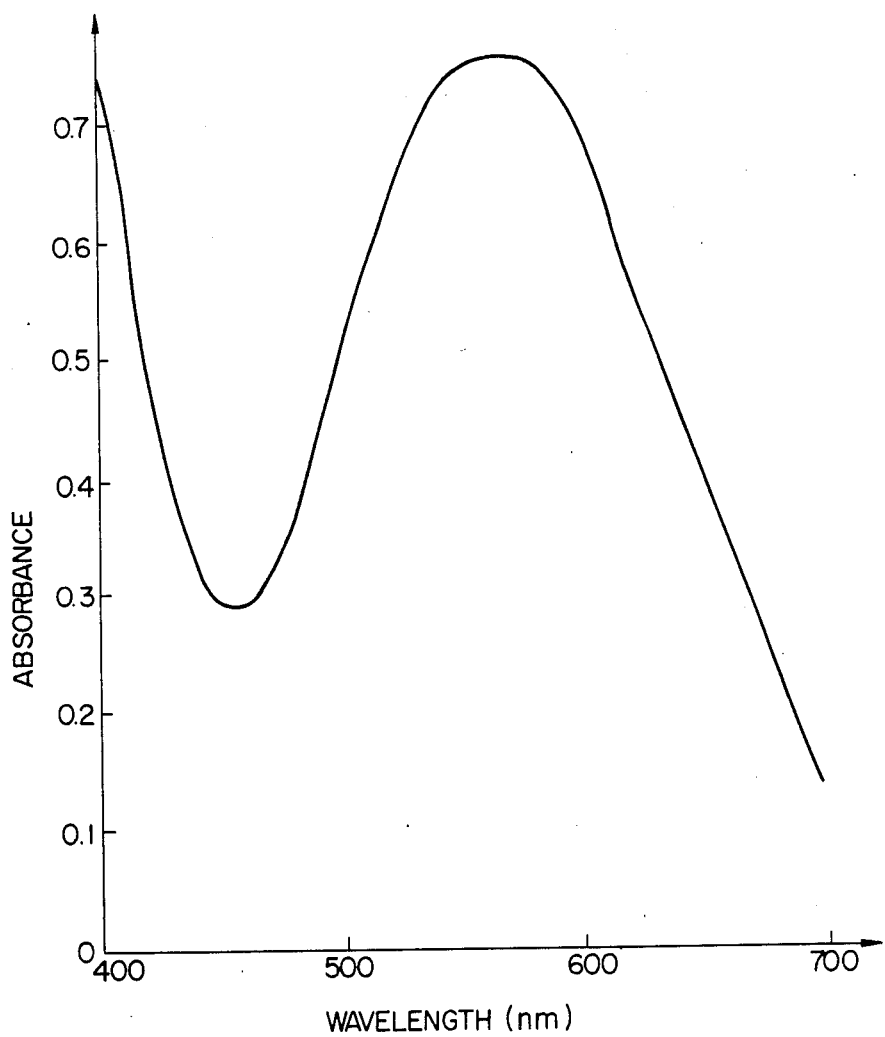
FIG. 5 is a graph showing an absorption curve.

The absorption curve is shown in FIG. 5. As is clear from FIG. 5, the sensitivity of superoxide ion is high.

EXAMPLE 1

Quantitative determination of free cholesterol in blood serum

Reagents (1) Standard solutions
Standard solutions are prepared by dissolving 40 mg, 80 mg, 120 mg, 160 mg and 200 mg of cholesterol in isopropanol and making the volume 100 ml, respectively.

(2) Color producing reagent solution
In 0.1M tris buffer solution (pH 8.0), 150 units of cholesterol oxidase, 100 mg of GSH, 6000 units of peroxidase, 1 g of phenol, 20 mg of potassium cyanide and 200 mg of $NO_2$-TB are dissolved and the whole volume is made 1000 ml.

Measuring Method

To 50 μl of blood serum, 4.0 ml of the color producing reagent solution is added and incubated in a constant temperature chamber at 37° C. for 10 minutes. Absorbance at wavelength of 560 nm is measured by using reagent blank as control.

On the other hand, using the standard solutions containing cholesterol in amounts 40, 80, 120, 160 and 200 mg/dl, the calibration curve is prepared from absorbances measured in the same manner as mentioned above. The content of free cholesterol in blood serum is determined using said calibration curve.

The results are shown in Table 3.

TABLE 3

| Serum No. | Amount (mg/dl) |
|---|---|
| 1 | 44.7 |
| 2 | 51.0 |
| 3 | 66.2 |
| 4 | 49.3 |
| 5 | 36.8 |
| Average | 49.6 |

The above-mentioned process can be applied to other substrates such as glucose, glycerol, glycerol phosphate, choline, acyl CoA, pyruvic acid, uric acid, xanthine and lactic acid. In such cases, individual specific oxidases corresponding to substrates to be determined are used in place of cholesterol oxidase in the case of determination of cholesterol.

In the above-mentioned process, peroxidase is used, but the same effects can be obtained by using iron complex of porphyrin or iron chelate in place of peroxidase.

That is, a substrate to be measured is treated with an oxidase (a) which has a specificity to said substrate, and the generated superoxide ion quantitatively from the enzymic reaction is measured by applying its reducing properties to quantitatively determine the substrate. In such a case, (b') iron complex of porphyrin or iron chelate, (c) an amine and/or a phenol, (d) a thiol compound and (e) a color producing reagent to be reduced are used for improving the measuring time, sensitivity, quantitativeness and the like, which properties are necessary for practical application of this invention. Thus, the reaction rates of the enzymic reaction of oxidase (i.e. the formation of superoxide ion) and the reducing reaction of the superoxide ion against the color producing reagent to be reduced can be accelerated effectively, quantitative determination of superoxide ion (or in other words, quantitative determination of substrate) which is generated by treating a substrate with an oxidase can be improved in quantitativeness, and requirements for the measuring time and sensitivity can be satisfied sufficiently.

Further, in order to remove autooxidation which is an undesirable side reaction at the time of measurement and probably caused by the thiol compound and the like additives, the addition of a chelating agent is preferable in order to proceed the desired reaction stably. That is, a reagent composition comprising (a) an oxidase, (b') iron complex of porphyrin or iron chelate, (c) an amine and/or a phenol, (d) a thiol compound, (e) a color producing reagent to be reduced and (f) a chelating agent is used for such a purpose.

The process of this invention can be carried out as follows.

For example, to 0.1M of tris (precisely tris-HCl) buffer solution (pH 8.0), there are dissolved $2.5 \times 10^{-5}$ mole of cytochrome C, 15 units/dl of cholesterol oxidase, 1 mg/dl of hemin, and 0.1% by weight of phenol. To the resulting solution, a solution obtained by dissolving 0.8% by weight of glutathione (reduced form) in the same buffer solution as mentioned above is added. To the resulting mixture, isopropanol containing 200 mg/dl of cholesterol is added and incubated at 37° C. for, e.g. 10 minutes. Cytochrome C forms color and absorbance at a wavelength of 550 nm using the reagent blank as control (i.e., O.D. (−B1)) is 0.10. When only isopropanol is used in place of the iropropanol solution containing cholesterol, there is no color formation of cytochrome C. Further, the same results are obtained when 2,2'-di(4-nitrophenyl)-5,5'-diphenyl-3,3'-(3,3'-dimethoxy-4,4'-diphenylene)ditetrazolium chloride (hereinafter referred to as "NO$_2$-TB") is used as color producing reagent to be reduced. These color formation are found to be damaged by the presence of a large amount of superoxide dismutase which functions specifically to superoxide ion. That is, the color formation used in this invention is admitted to be caused by the reducing action of superoxide ion.

Oxidases are oxidizing enzymes and there are specific oxidases corresponding to individual substrates. Substrates and corresponding specific oxidases usable in this invention can be listed as follows:

| | |
|---|---|
| Glucose | Glucose oxidase |
| Cholesterol | Cholesterol oxidase |
| Glycerol | Glycerol oxidase |
| Glycerolphosphate | Glycerolphosphate oxidase |
| Choline | Choline oxidase |
| Acyl CoA | Acyl CoA oxidase |
| Pyruvic acid | Pyruvate oxidase |
| Uric acid | Uricase |
| Xanthine | Xanthine oxidase |
| Lactic acid | Lactate oxidase |

These oxidases can be obtained from living bodies producing these oxidases and can be available commercially.

As the iron complex of porphyrin, there can be used hemin, $\alpha,\beta,\gamma,\delta$-tetraphenylporphyrintrisulfonic acid-iron complex, $\alpha,\beta,\gamma,\delta$-tetrakis(4-N-methylpyridyl)porphyrin-iron complex, tetra-phenylporphyrin-iron complex, octaethylphorphyrin-iron complex, etc. The iron complex of porphyrin can be used in an amount of 0.007 to 0.06 mM/l in the reaction solution at the stage of color formation.

As the iron chelate, there can be used iron chelates of complexanes such as ethylenediaminetetraacetic acid (EDTA), diaminopropanetetraacetic acid, trans-cyclohexanediaminetetraacetic acid, hydroxyethylethylenediaminetriacetic acid, glycol ether diaminetetraacetic acid, etc. Among them, the use of EDTA.-Fe(III) is particularly preferable. The iron chelate of complexane can be used in an amount of 0.01 to 0.07 mM/l in the reaction solution at the stage of color formation.

As the amine, there can be used conventional organic amines. Aromatic amines are more effective than aliphatic amines with a small using amount. There can be used primary amines, secondary amines and tertiary amines. Examples of these amines are aniline, N-ethylaniline, N,N-dimethylaniline, N,N-diethylaniline, N,N-diethyl-m-toluidine, N-ethyl-N-$\beta$-hydroxyethyl-m-toluidine, 3,5-dimethoxy-N-ethyl-N-(2-hydroxy-3-sodium sulfopropyl)aniline and the like. The amine can be used in an amount of 0.0001% to 0.2% by weight in the reaction solution at the stage of color formation.

The phenol is not particularly influenced by other substituents. As the phenol, there can be used phenol, chlorophenols, dichlorophenols, naphthols, sulfonic acid derivatives and the like. The phenol can be used in an amount of 0.0001% to 0.2% by weight in the reaction solution at the stage of color formation.

A phenol and an amine can be used together. Further, there can be used a compound which belongs to phenols and also to amines, for example, 1-N,N-dimethylamino-4-naphthol, 4-N,N-diethylaminosalicylic acid, or the like. But in the case of an amine, L-amino acid, or the like substrate and amine oxidase, L-amino acid oxidase, or the like oxidase, the use of phenol, not amine, is, needless to say, preferable.

As the thiol compound having a SH group, there can be used reduced glutathione, thioglycolic acid, mercaptoethanol, thiosalicylic acid, cysteamine, cysteine, dimercaptosuccinic acid, etc. The thiol compound can be used in an amount of 1 to 50 mg/dl in the reaction solution at the stage of color formation.

The color producing reagent to be reduced means a reagent which has a suitable oxidation reduction potential and produces color by the reduction with superoxide ion. Examples of the color producing reagent to be reduced are tetrazolium salts such as $NO_2$-TB, 2-(4-iodophenyl)-3-(4-nitrophenyl)-5-phenyltetrazolium chloride (hereinafter referred to as "INT"), 3-(4,5-dimethylthiazolyl-2)-2,5-diphenyltetrazolium bromide (hereinafter referred to as "MTT"), etc.; cytochrome C, tetranitromethane (very dangerous), plastocyanin, Blue protein, etc. The color producing reagent to be reduced can be used in an amount of 1 to 40 mg/dl in the reaction solution at the stage of color formation. The tetrazolium compounds had various problems in that formazans produced by reduction of tetrazolium compounds are difficultly soluble in water, quantitativeness of color formation is not good, and devices are contaminated, and the like, but recent development obtained by introducing a group which improves the solubility into tetrazolium compounds solved such problems and makes it possible to employ these compounds in this invention.

As the chelating agent, there can be used ethylenediaminetetraacetic acid (EDTA), trans-cyclohexanediaminetetraacetic acid or trans-1,2-cyclohexanediamine-N,N,N',N'-tetraacetic acid (CyDTA), diethylenetriaminepentaacetic acid or diethylenetriamine-N,N,N',N'-pentaacetic acid (DTPA), etc. The chelating agent can be used in an amount of 0.5 to 5 millimol/dl (mM/dl) in the reaction solution at the stage of color formation. The addition of the chelating agent makes the variation of reagent blank values small.

In the case of using the above-mentioned compounds in proper combination, if the final mixture to be measured on its coloring is clouded so as to damage the measurement, a surface active agent or solubility aid can be added thereto according to a conventional process.

The presence of anticoagulants such as heparin, sodium citrate, sodium oxalate, etc., and glycolytic inhibitors such as sodium fluoride, etc., do not influence the color formation according to the process and reagents of this invention. Further, the presence of ascorbic acid, bilirubin, hemoglobin, uric acid, pyruvic acid, glucose and the like which are present in a living body physiologically, or pathologically, or by the dosage for treatment, do not influence the color formation according to the process and reagents of this invention because of specificity of individual oxidases for objected substrates.

In practical measurement, to a sample to be tested, a mixture of (a) a special oxidase for a substrate to be determined, (b') iron complex of porphyrin or iron chelate, (c) an amine and/or a phenol, (d) a thiol compound, and (e) a color producing reagent to be reduced, and if necessary for better results, (f) a chelating agent is added in a suitable medium (usually in a buffer solution) and incubated so as to proceed the desired reaction to a desired degree, and the resulting color formation or color change is measured to quantitatively determine the substrate content in the sample. For such a purpose, the oxidase and the like additives and reagents are mixed into one or into several groups or can be used alone. Various combinations of the above-mentioned additives and reagents, alone or as a mixture thereof, are possible for providing the reagents used in the process of this invention. The medium for the reagents or the reaction solution is preferably made pH 7.0 or higher, more preferably 7.5 or higher, during the determination.

As mentioned above, this invention provides a process and a mixture of reagents for quantitative determination of a substrate in body fluid component wherein superoxide ion is measured. Such an invention is epoch-making and contributes to this field of art greatly.

The following Examples further illustrate this invention.

EXAMPLE 2

(Cholesterol)

A color producing reagent solution is prepared by dissolving in 0.1M tris buffer solution (pH 8.0) 20 mg/dl of $NO_2$-TB, 1.06 mM/l of phenol, 0.65 mM/l of reduced glutathione, 1 mg/dl of hemin, 15 U/dl of cholesterol oxidase and 0.1 g/dl of Triton X-100 (octylphenoxypolyethoxyethanol—available from Rohm and Haas Co.). On the other hand, a sample solution to be tested is prepared by dissolving 200 mg of cholesterol in isopropanol and making the volume 100 ml.

To 50 µl of the sample solution, 3.0 ml of the color producing solution is added and incubated in a constant temperature chamber at 37° C. for 10 minutes. Then, absorbance at wavelength of 560 nm is measured using reagent blank as control.

REFERENCE EXAMPLE 1

(Cholesterol)

In the color producing reagent solution used in Example 2, 300 U/dl of peroxidase is used in place of hemin. Absorbance is measured in the same manner as described in Example 2 using the resulting color producing reagent solution.

COMPARATIVE EXAMPLE 1

(Cholesterol)

In the color producing reagent solution used in Example 2, hemin is not added. Using the resulting color producing reagent solution, absorbance is measured in the same manner as described in Example 2.

The results are shown in Table 4. As is clear from Table 4, hemin has the same effect or higher effect compared with peroxidase.

TABLE 4

| Example No. | Example 2 | Reference Example 1 | Comparative Example 1 |
|---|---|---|---|
| Absorbance | 1.391 | 1.286 | 0.264 |

EXAMPLE 3

(Cholesterol)

In the color producing reagent solution used in Example 2, 1 mg/dl of EDTA.Fe(III) is used in place of hemin. Using the resulting color producing reagent solution, absorbance is measured in the same manner as described in Example 2.

The results are shown in Table 5. As is clear from Table 5, EDTA. Fe(III) has the same effect as peroxidase.

TABLE 5

| Example No. | Example 3 | Reference Example 1 | Comparative Example 1 |
|---|---|---|---|
| Absorbance | 1.264 | 1.286 | 0.264 |

COMPARATIVE EXAMPLE 2

(Cholesterol)

In the color producing reagent solution used in Example 2, 1 mg/dl of 2 Na-EDTA is used in place of hemin. Using the resulting color producing reagent solution, absorbance is measured in the same manner as described in Example 2.

The results are shown in Table 6. As is clear from Table 6, no effect is obtained by 2 Na-EDTA.

TABLE 6

| Example No. | Comparative Example 2 | Example 3 | Comparative Example 1 |
|---|---|---|---|
| Absorbance | 0.258 | 1.264 | 0.264 |

COMPARATIVE EXAMPLE 3

(Cholesterol)

In the color producing reagent solution used in Example 2, 1 mg/dl of EDTA.Ni(II) or EDTA.Mn(II) is used in place of hemin. Using the resulting color producing reagent solution, absorbance is measured in the same manner as described in Example 2.

The results are shown in Table 7. As is clear from Table 7, almost no effect is admitted compared with Example 3.

TABLE 7

| Example No. | Comparative EDTA.Ni (II) | Example 3 EDTA.Mn (II) | Example 3 | Comparative Example 1 |
|---|---|---|---|---|
| Absorbance | 0.273 | 0.275 | 1.264 | 0.264 |

EXAMPLE 4

(Cholesterol)

In the color producing reagent solution used in Example 2, 1 mg/dl of diaminopropanetetraacetic acid-iron(III)(Methyl-EDTA.Fe(III)), trans-cyclohexanediaminetetraacetic acid-iron(III)(CyDTA.Fe(III)), or hydroxyethylethylenediaminetriacetic acid-iron(III)-(EDTA-OH. Fe(III)) is used in place of hemin. Using the resulting color producing reagent solution, absorbance is measured in the same manner as described in Example 2.

The results are shown in Table 8. As is clear from Table 8, effects of addition of iron chelates are remarkable compared with Comparative Example 1.

TABLE 8

| Example No. | Absorbance |
|---|---|
| Example 4 | |
| Methyl-EDTA.Fe (III) | 0.979 |

TABLE 8-continued

| Example No. | Absorbance |
|---|---|
| CyEDTA.FE (III) | 0.501 |
| EDTA-OH.Fe (III) | 0.400 |
| Comparative Example 1 | 0.264 |

EXAMPLE 5

(Acyl CoA)

A color producing reagent solution is prepared by dissolving in 0.1M tris buffer solution (pH 8.0) 10 mg/dl of $NO_2$-TB, 1.06 mM/l of phenol, 1 mg/dl of hemin, 20 mg/dl of reduced glutathione, and 240 U/dl of acyl CoA oxidase. On the other hand, a sample solution to be tested is prepared by dissolving in distilled water 2 mM of palmitoyl CoA and making the volume 100 ml.

To 100 $\mu$l of the sample solution, 3.0 ml of the color producing reagent solution is added and incubated in a constant temperature chamber at 37° C. for 10 minutes. Then, absorbance at wavelength of 560 nm is measured using reagent blank as control.

REFERENCE EXAMPLE 2

(Acyl CoA)

In the color producing reagent solution used in Example 5, 600 U/dl of peroxidase is used in place of hemin. Using the resulting color producing reagent solution, absorbance is measured in the same manner as described in Example 5.

The results are shown in Table 9. As is clear from Table 9, hemin has the same effect or higher effect compared with peroxidase.

TABLE 9

| Example No. | Example 5 | Reference Example 2 |
|---|---|---|
| Absorbance | 1.100 | 0.997 |

EXAMPLE 6

(Glucose)

A color producing reagent solution is prepared by dissolving in 0.1M phosphate buffer solution (pH 8.0) 10 mg/dl of INT, 0.1% by weight of 3,5-dimethoxy-N-ethyl-N-(2-hydroxy-3-sodium sulfopropyl)aniline, 1 mg/dl of hemin, 20 mg/dl of reduced glutathion, and 3000 U/dl of glucose oxidase. On the other hand, a sample solution is prepared by dissolving in distilled water 200 mg/dl of glucose.

To 20 $\mu$l of the sample solution, 3.0 ml of the color producing reagent solution is added and incubated in a constant temperature chamber at 37° C. for 10 minutes. Then, absorbance at wavelength of 500 nm is measured using reagent blank as control.

REFERENCE EXAMPLE 3

(Glucose)

In the color producing reagent solution used in Example 6, 600 U/dl of peroxidase is used in place of hemin. Using the resulting color producing reagent solution, absorbance is measured in the same manner as described in Example 6.

The results are shown in Table 10. As is clear from Table 10, hemin has the same effect or higher effect compared with peroxidase.

TABLE 10

| Example No. | Example 6 | Reference Example 3 |
|---|---|---|
| Absorbance | 1.095 | 1.000 |

EXAMPLE 7

(Pyruvic acid)

A color producing reagent solution is prepared by dissolving in 0.02M phosphate buffer solution (pH 7.1) 20 mg/dl of $NO_2$-TB, 1.06 mM/l of phenol, 1 mg/dl of hemin, 10 mg/dl of reduced glutathione, 700 U/dl of pyruvate oxidase, 2 mg/dl of flavin adenine dinucleotide, 44 mg/dl of thiamine pyrophosphate, and 0.15% by weight of magnesium acetate. On the other hand, a sample solution to be tested is prepared by dissolving lithium pyruvate in an amount of 10 mg/dl as pyruvic acid in distilled water.

To 100 μl of the sample solution, 3.0 ml of the color producing reagent solution is added and incubated in a constant temperature chamber at 37° C. for 15 minutes. Then, absorbance at wavelength of 560 nm is measured using reagent blank as control to obtain the value of 0.050.

EXAMPLE 8

(Choline)

A color producing reagent solution is prepared by dissolving in 0.1M tris buffer solution (pH 8.0) 10 mg/dl of $NO_2$-TB, 1.06 mM/l of phenol, 1 mg/dl of hemin, 10 mg/dl of thiosalicylic acid, and 500 U/dl of choline oxidase. On the other hand, a sample solution to be tested is prepared by dissolving 70 mg/dl of choline chloride in distilled water.

To 20 μl of the sample solution, 3.0 ml of the color producing reagent solution is added and incubated in a constant temperature chamber at 37° C. for 10 minutes. Then, absorbance at wavelength of 560 nm is measured using reagent blank as control.

REFERENCE EXAMPLE 4

(Choline)

In the color producing reagent solution used in Example 8, 600 U/dl of peroxidase is used in place of hemin. Using the resulting color producing reagent solution, absorbance is measured in the same manner as described in Example 8.

The results are shown in Table 11. As is clear from Table 11, hemin has the same effect or higher effect compared with peroxidase.

TABLE 11

| Sample No. | Example 8 | Reference Example 4 |
|---|---|---|
| Absorbance | 1.191 | 1.100 |

EXAMPLE 9

(Glycerol-3-phosphate)

A color producing reagent solution is prepared by dissolving in 0.1M tris buffer solution (pH 8.0) 10 mg/dl of $NO_2$-TB, 0.5 mM/l of phenol, 1 mg/dl of hemin, 20 mg/dl of reduced glutathione, and 600 U/dl of glycerol-3-phosphate oxidase. On the other hand, a sample solution is prepared by dissolving 10 mM (172 mg/dl) of glycerol-3-phosphate in distilled water.

To 50 μl of the sample solution, 4.0 ml of the color producing reagent solution is added and incubated in a constant temperature chamber at 37° C. for 10 minutes. Then, absorbance at wavelength of 560 nm is measured using reagent blank as control.

REFERENCE EXAMPLE 5

(Glycerol-3-phosphate)

In the color producing reagent solution used in Example 9, 600 U/dl of peroxidase is used in place of hemin. Using the resulting color producing reagent solution, absorbance is measured in the same manner as described in Example 9.

The results are shown in Table 12. As is clear from Table 12, hemin has the same effect or higher effect compared with peroxidase.

TABLE 12

| Sample No. | Example 9 | Reference Example 5 |
|---|---|---|
| Absorbance | 0.725 | 0.678 |

EXAMPLE 10

(Glycerol)

A color producing reagent solution is prepared by dissolving in 0.05M phosphate buffer solution (pH 8.0) 10 mg/dl of $NO_2$-TB, 0.5 mM/l of phenol, 1 mg/dl of hemin, 20 mg/dl of reduced glutathione, and 600 U/dl of glycerol oxidase. On the other hand, a sample solution is prepared by dissolving 2 mM of glycerin in distilled water and making the volume 100 ml.

To 50 μl of the sample solution, 4.0 ml of the color producing reagent solution is added and incubated in a constant temperature chamber at 37° C. for 10 minutes. Then, absorbance at wavelength of 560 nm is measured using reagent blank as control.

REFERENCE EXAMPLE 6

(Glycerol)

In the color producing reagent solution used in Example 10, 600 U/dl of peroxidase is used in place of hemin. Using the resulting color producing reagent solution, absorbance is measured in the same manner as described in Example 10.

The results are shown in Table 13. As is clear from Table 13, hemin has the same or higher effect compared with peroxidase.

TABLE 13

| Sample No. | Example 10 | Reference Example 6 |
|---|---|---|
| Absorbance | 0.090 | 0.081 |

EXAMPLE 11

(Uric acid)

A color producing reagent solution is prepared by dissolving in 0.1M tris buffer solution (pH 7.1) 20 mg/dl of $NO_2$-TB, 1.06 mM/l of phenol, 1 mg/dl of hemin, 10 mg/dl of reduced glutathione, and 30 U/dl of uricase. On the other hand, a sample solution to be tested is prepared by dissolving uric acid in an amount of 10 mg/dl in a 1% aqueous solution of lithium carbonate.

To 60 μl of the sample solution, 3.0 ml of the color producing reagent solution is added and incubated in a constant temperature chamber at 37° C. for 10 minutes. Then, absorbance at wavelength of 560 nm is measured using reagent blank as control.

REFERENCE EXAMPLE 7

(Uric acid)

In the color producing reagent solution used in Example 11, 600 U/dl of peroxidase is used in place of hemin. Using the resulting color producing reagent solution, absorbance is measured in the same manner as described in Example 11.

The results are shown in Table 14. As is clear from Table 14, hemin has the same or higher effect compared with peroxidase.

TABLE 14

| Example No. | Example 11 | Reference Example 7 |
|---|---|---|
| Absorbance | 0.081 | 0.074 |

EXAMPLE 12

(L-Lactic acid)

A color producing reagent solution is prepared by dissolving in 0.1M tris buffer solution (pH 7.5) 20 mg/dl of $NO_2$-TB, 1.06 mM/l of phenol, 1 mg/dl of hemin, 10 mg/dl of reduced glutathione, and 85 U/dl of L-lactic acid oxidase. On the other hand, a sample solution is prepared by dissolving 10 mM of sodium L-lactate in distilled water and making the volume 100 ml.

To 50 μl of the sample solution, 3.0 ml of the color producing reagent solution is added and incubated in a constant temperature chamber at 37° C. for 10 minutes. Then, absorbance at wavelength of 560 nm is measured using reagent blank as control.

REFERENCE EXAMPLE 8

(L-Lactic acid)

In the color producing reagent solution used in Example 12, 600 U/dl of peroxidase is used in place of hemin. Using the resulting color producing reagent solution, absorbance is measured in the same manner as described in Example 12.

The results are shown in Table 15. As is clear from Table 15, hemin has the same or higher effect compared with peroxidase.

TABLE 15

| Example No. | Example 12 | Reference Example 8 |
|---|---|---|
| Absorbance | 0.122 | 0.110 |

EXAMPLE 13

(Free cholesterol in blood serum)

A color producing reagent solution is prepared by dissolving in 0.1M tris buffer solution (pH 8.0) 20 mg/dl of $NO_2$-TB, 2 mM/l of phenol, 0.65 mM/l of reduced glutathione, 0.017 mM/l of EDTA.Fe(III), 15 U/dl of cholesterol oxidase and 0.1 g/dl of Triton X-100.

To 50 μl of blood serum, 3.0 ml of the color producing reagent solution is added and incubated in a constant temperature chamber at 37° C. for 10 minutes. Then, absorbance at wavelength of 560 nm is measured using reagent blank as control.

The cholesterol content in the sample is calculated by the calibration curve obtained previously.

REFERENCE EXAMPLE 9

(Free cholesterol in blood serum)

A color producing reagent solution is prepared by dissolving in 0.1M phosphate buffer solution (pH 7.0) 0.1% by weight of phenol, 0.01% by weight of 4-aminoantipyrine, 10 U/dl of cholesterol oxidase, 300 U/dl of peroxidase, and 0.15% by weight of Triton X-100.

To 50 μl of blood serum, 3.0 ml of the color producing reagent solution is added and incubated in a constant temperature chamber at 37° C. for 15 minutes. Then, absorbance at wavelength of 505 nm is measured using reagent blank as control.

The cholesterol content in the sample is calculated by the calibration curve obtained previously.

As shown in Table 16, the values obtained in Example 13 and Reference Example 9 are in good agreement and no significant difference is admitted.

TABLE 16

| Blood serum No. | Example 13 X | | Reference Example 9 Y | |
|---|---|---|---|---|
| 1 | 46 | mg/dl | 47 | mg/dl |
| 2 | 40 | | 40 | |
| 3 | 38 | | 37 | |
| 4 | 59 | | 61 | |
| 5 | 34 | | 35 | |
| 6 | 52 | | 50 | |
| 7 | 55 | | 56 | |
| 8 | 81 | | 81 | |
| 9 | 32 | | 33 | |
| 10 | 43 | | 41 | |
| Average | 48.0 | | 48.1 | |
| S.D. | 14.6 | | 14.7 | | r = 0.996
Y = 1.00X − 0.13

EXAMPLE 14

(Free cholesterol in blood serum)

In the color producing reagent solution used in Example 13, 2.5 mM/l of EDTA.Fe(III) is used in place of 0.017 mM/l of EDTA.Fe(III).

To 50 μl of the sample solution used in Example 13, 3.0 ml of the above-mentioned color producing reagent solution is added and incubated in a constant temperature chamber at 37° C. for 10 minutes. Then, absorbance of the sample ($E_S$) and that of reagent blank ($E_{BL}$) are measured using water as control.

The results are shown in Table 17. As is clear from Table 17, effects of addition of EDTA.Fe(III) are admitted.

TABLE 17

| | Addition of EDTA.Fe (III) | | | No addition of EDTA.Fe (III) | | |
|---|---|---|---|---|---|---|
| | $E_S$ | $E_{BL}$ | $E_S - E_{BL}$ | $E_S$ | $E_{BL}$ | $E_S - E_{BL}$ |
| Absorbance | 1.458 | 0.198 | 1.260 | 1.563 | 0.299 | 1.264 |

EXAMPLE 15

(Cholesterol)

A color producing reagent solution is prepared by dissolving in 0.1M tris buffer solution (pH 8.0) 20 mg/dl of $NO_2$-TB, 1.06 mM/l of a phenol or amine compound listed in Table 18, 0.65 mM/l of reduced glutathione, 1 mg/dl of EDTA.Fe(III), 15 U/dl of cholesterol oxidase, 0.1 g/dl of Triton X-100 and 0.4 g/dl of Emulgen 920. On the other hand, a sample solution to be tested is prepared by dissolving 200 mg of cholesterol in isopropanol and making the volume 100 ml.

To 50 μl of the sample solution, 3.0 ml of the color producing reagent solution is added and incubated in a constant temperature chamber at 37° C. for 10 minutes. Then, absorbance at wavelength of 560 nm is measured using reagent blank as control.

The results are shown in Table 18. Table 18 clearly shows the effect of addition of phenols and amines.

TABLE 18

| Amine or phenol | O.D. (-Bl) |
| --- | --- |
| No addition | 0.38 |
| Phenol | 1.26 |
| p-Chlorophenol | 1.26 |
| o-Chlorophenol | 1.26 |
| m-Chlorophenol | 1.25 |
| 2,4,6-Trichlorophenol | 1.25 |
| Aniline | 1.28 |
| N—Ethylaniline | 1.28 |
| N,N—Diethylaniline | 1.27 |
| N,N—Dimethyl-m-toluidine | 1.28 |
| N—Ethyl—N—β-hydroxyethyl-m-toluidine | 1.28 |
| 4-N,N—Diethylaminosalicylic acid | 1.20 |
| 1-N,N—Dimethylaminonaphthalene 7-sulfonic acid | 1.23 |
| 1-Naphthol-8-sulfonic acid | 1.10 |

EXAMPLE 16

(Cholesterol)

A color producing reagent solution is prepared by dissolving in 0.1M tris buffer solution (pH 8.0) 20 mg/dl of $NO_2$-TB, 1.06 mM/l of phenol, 0.65 mM/l of thiol compound as listed in Table 19, 1 mg/dl of EDTA.-Fe(III), and 15 U/dl of cholesterol oxidase. On the other hand, a sample solution to be tested is prepared by dissolving 200 mg of cholesterol in isopropanol and making the volume 100 ml.

To 50 μl of the sample solution, 3.0 ml of the color producing reagent solution is added and incubated in a constant temperature chamber at 37° C. for 10 minutes. Then, absorbance at wavelength of 560 nm is measured using reagent blank as control.

The results are shown in Table 19. Table 19 clearly shows the effect of addition of thiol compounds.

TABLE 19

| Thiol compound | O.D. (-Bl) |
| --- | --- |
| No addition | 0.03 |
| Glutathione (reduced form) | 1.26 |
| Thioglycolic acid | 1.27 |
| L—Cysteine | 2.24 |
| Cysteamine | 1.59 |
| Thiosalicylic acid | 1.26 |

TABLE 19-continued

| Thiol compound | O.D. (-Bl) |
| --- | --- |
| Dimercaptosuccinic acid | 1.03 |

What is claimed is:

1. A process for quantitatively determining a substrate, which comprises treating a sample containing a substrate with a specific oxidase corresponding to said substrate and measuring the generated superoxide ion, said oxidase treatment and measuring of generated superoxide ion conducted by measuring color formation or color change being conducted by using a reagent composition comprising (a) the specific oxidase corresponding to the substrate to be determined, (b) iron complex of porphyrin or iron chelate, (c) an amine and/or a phenol, (d) a thiol compound in an amount effective to retard the conversion of superoxide into hydrogen peroxide, and (e) a color producing reagent to be reduced.

2. A process according to claim 1, wherein the substrate is one member selected from the group consisting of glucose, cholesterol, glycerol, glycerol phosphate, choline, acyl CoA, pyruvic acid, uric acid, xanthine and lactic acid.

3. A process for quantitatively determining a substrate, which comprises treating a sample containing a substrate with a specific oxidase corresponding to said substrate and measuring the generated superoxide ion, said oxidase treatment and measuring of generated superoxide ion conducted by measuring color fomation or color change being conducted by using a reagent composition comprising (a) the specific oxidase corresponding to the substrate to be determined, (b) iron complex of porphyrin or iron chelate, (c) an amine and/or a phenol, (d) a thiol compound in an amount effective to retard the conversion of superoxide into hydrogen peroxide, (e) a color producing reagent to be reduced, and (f) a chelating agent.

4. A process according to claim 3, wherein the substrate is one member selected from the group consisting of glucose, cholesterol, glycerol, glycerol phosphate, choline, acyl CoA, pyruvic acid, uric acid, xanthine and lactic acid.

5. A composition for quantitative determination of a substrate comprising in a mixture (a) a specific oxidase corresponding to a substrate to be determined, (b') iron complex of porphyrin or iron chelate, (c) an amine and/or a phenol, (d) a thiol compound in an amount effective to retard the conversion of superoxide into hydrogen peroxide, and (e) a color producing reagent to be reduced, the components of the mixture being present in amounts effective for quantitatively determining a substrate.

6. A composition for quantitative determination of a substrate comprising in a mixture (a) a specific oxidase corresponding to a substrate to be determined, (b) iron complex of porphyrin or iron chelate, (c) an amine and/or a phenol, (d) a thiol compound in an amount effective to retard the conversion of superoxide into hydrogen peroxide, (e) a color producing reagent to be reduced and (f) a chelating agent, the components of the mixture being present in amounts effective for the quantitative determination of a substrate.

* * * * *